(12) United States Patent
Nakamura

(10) Patent No.: US 8,585,633 B2
(45) Date of Patent: *Nov. 19, 2013

(54) GAS MIST PRESSURE BATH SYSTEM

(75) Inventor: Shoichi Nakamura, Higashichikuma-gun (JP)

(73) Assignee: ACP Japan, Higashichikuma-Gun, Nagano (JP)

( * ) Notice: Subject to any disclaimer, the term of this patent is extended or adjusted under 35 U.S.C. 154(b) by 285 days.

This patent is subject to a terminal disclaimer.

(21) Appl. No.: 12/998,581

(22) PCT Filed: Feb. 16, 2010

(86) PCT No.: PCT/JP2010/052239
§ 371 (c)(1),
(2), (4) Date: May 5, 2011

(87) PCT Pub. No.: WO2010/095607
PCT Pub. Date: Aug. 26, 2010

(65) Prior Publication Data
US 2011/0208116 A1   Aug. 25, 2011

(30) Foreign Application Priority Data

Feb. 19, 2009  (JP) ................................. 2009-037109
Feb. 19, 2009  (JP) ................................. 2009-037110

(51) Int. Cl.
*A61M 37/00*  (2006.01)
(52) U.S. Cl.
USPC .......................................................... 604/23
(58) Field of Classification Search
USPC ............. 604/23, 24; 607/83, 84, 91; 601/151, 601/152
See application file for complete search history.

(56) References Cited

U.S. PATENT DOCUMENTS

| 3,593,710 A | * | 7/1971 | Eichelman et al. ...... 128/200.11 |
| 3,908,704 A | * | 9/1975 | Clement et al. ............... 138/121 |
| 3,936,698 A | * | 2/1976 | Meyer ........................... 361/231 |

(Continued)

FOREIGN PATENT DOCUMENTS

| JP | S61-217132 | | 9/1986 |
| JP | H07-171189 | * | 7/1995 |

(Continued)

*Primary Examiner* — Kevin C Sirmons
*Assistant Examiner* — Deanna K Hall
(74) *Attorney, Agent, or Firm* — Manabu Kanesaka

(57) ABSTRACT

The invention to provide a gas mist pressure bath system which is possible to control the amounts, pressures and others of gas and liquid, and cause the gas mist to be absorbed through the skin and mucous membrane of a human living organism under an optimum condition. This system is for preparing a mist (gas mist) by pulverizing and dissolving a gas (carbon dioxide or oxygen, otherwise a mixed gas) and a liquid at a density of not less than a predetermined value, and contacting the mist to the skin and mucous membrane of a living organism. The system comprises a first gas supply means 11 for generating the gas mist, a second gas supply means 12 for dissolving the gas in the liquid, a liquid supply means 21, a gas mist supply means 31 for pressure-supplying the gas mist, and a covering member 41 for covering the skin and mucous membrane and forming a space for sealing inside the gas mist supplied from the gas mist supply means 31, contacting the gas mist within the living organism covering member 41 to the skin and mucous membrane at pressure of not less than a predetermined value.

20 Claims, 11 Drawing Sheets

(56) References Cited

U.S. PATENT DOCUMENTS

| | | | |
|---|---|---|---|
| 5,667,769 A * | 9/1997 | Kuckens et al. | 424/70.1 |
| 5,984,868 A * | 11/1999 | Shih et al. | 600/300 |
| 7,122,018 B2 * | 10/2006 | Stenzler et al. | 604/23 |
| 8,230,853 B2 * | 7/2012 | Nakamura | 128/202.12 |

FOREIGN PATENT DOCUMENTS

| | | |
|---|---|---|
| JP | H11-192421 | 7/1999 |
| JP | 2005-058745 | 3/2005 |
| JP | 2005-205163 | 8/2005 |
| JP | 2006-026022 | 2/2006 |
| JP | 2007-014482 | 1/2007 |
| JP | U 3144717 | 8/2008 |
| JP | U 3144718 | 8/2008 |

* cited by examiner

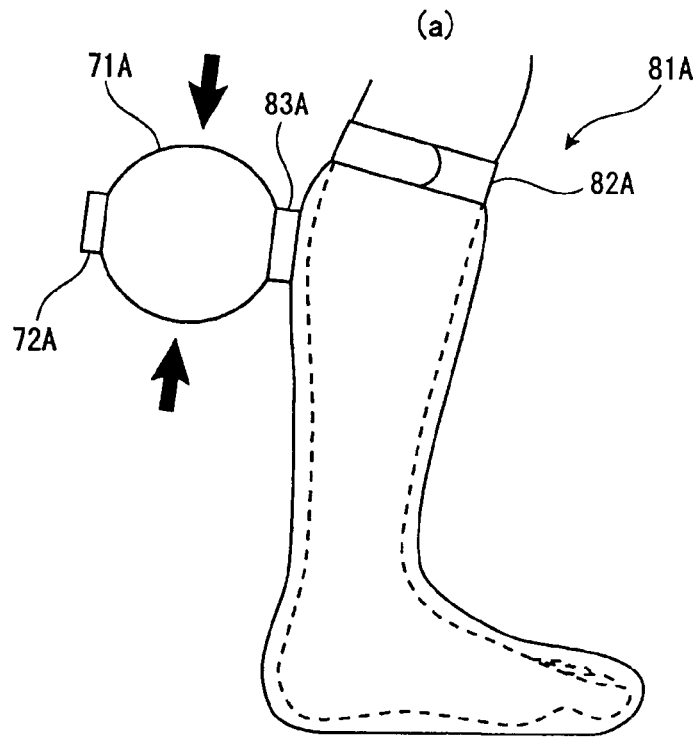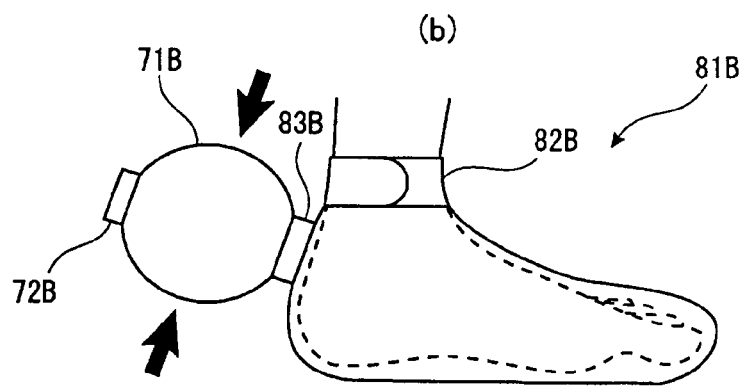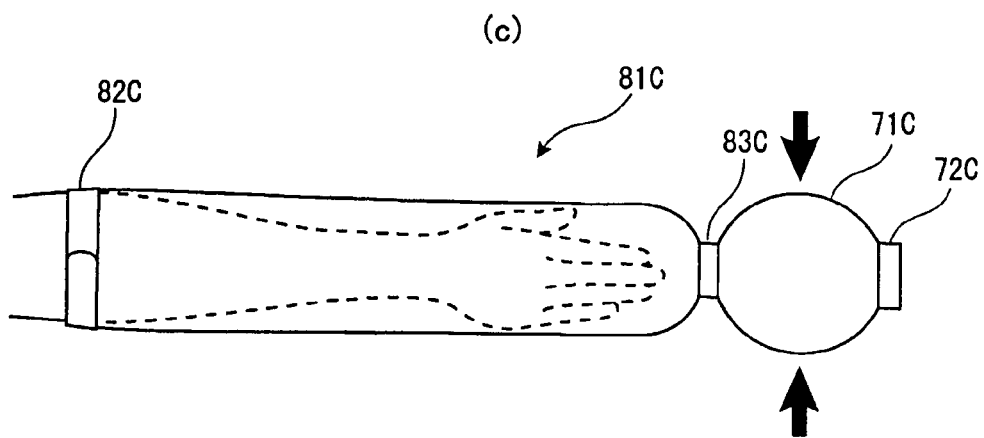
FIG. 9

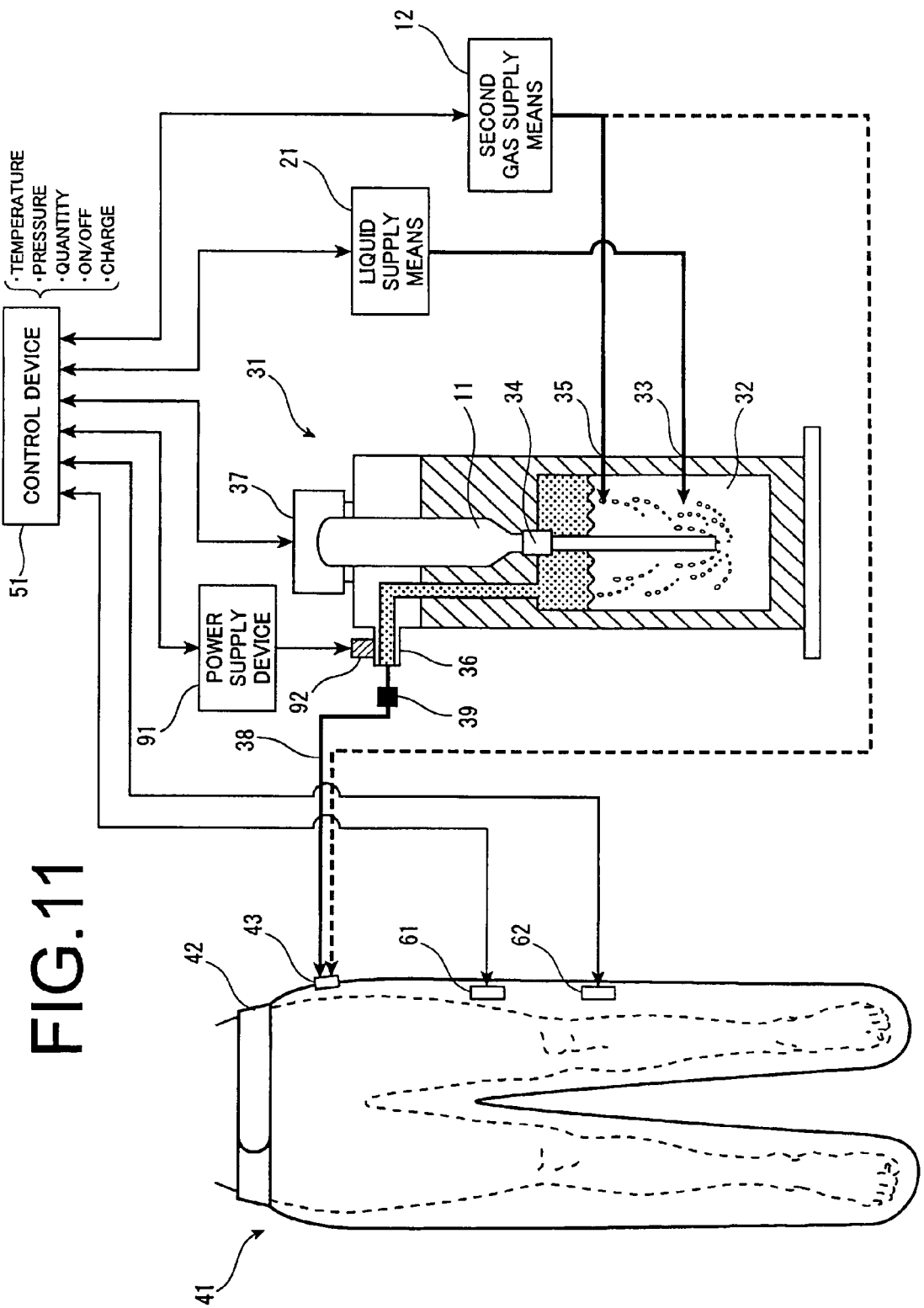

GAS MIST PRESSURE BATH SYSTEM

RELATED APPLICATIONS

The present application is National Phase of International Application No. PCT/JP2010/052239 filed Feb. 16, 2010, and claims priorities from, Japanese Applications No. 2009-037109 filed Feb. 19, 2009 and No. 2009-037110 filed Feb. 19, 2009, the disclosure of which are hereby incorporated by reference herein in its entirety.

TECHNICAL FIELD

The present invention relates to a gas mist pressure bath system, in which a mist (called as "gas mist" hereafter) is prepared by pulverizing and dissolving carbon dioxide or oxygen, otherwise a mixed gas (called as "gas" hereafter) of carbon dioxide and oxygen, and liquid, and the thus prepared gas mist is directly contacted to a skin and mucous membrane of a living organism at pressure of not less than a predetermined value, thereby to improve a gas absorption efficiency into the skin and mucous membrane.

BACKGROUND ART

It has conventionally been known that carbon dioxide (carbonic acid anhydride: $CO_2$) has both properties of being not only soluble in water (water-soluble) but also soluble in fat (fat-soluble) and, therefore, by only contacting the skin and mucous membrane of the living organism being like mixed with water and fat, carbon dioxide penetrates under a subcutaneous layer and expands blood vessels around the parts of penetrated carbon dioxide, and it works to improve the blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide seems to be a waste product resulted from action of the cell, however, it plays in fact very important roles in the living organism.

Further, in recent times, oxygen of the high density has also widely been known as effective inactivity of metabolism, accelerating the blood circulation, fatigue recovery, or stability of blood pressure. Other than them, oxygen has disinfection or sterilization by oxidative effect.

As a prior art for causing carbon dioxide to be absorbed into the living organism, a most broadly used technique is (1) a bathing agent generating carbon dioxide in water. Throwing this bathing agent into hot water in a bathtub, it generates carbon dioxide by reacting carbonate and acid contained in the bathing agent, and dissolves it in hot water. Carbon dioxide dissolved in hot water contacts the skin of a bathing person and penetrates his subcutaneous layer to display physiological effects as above mentioned.

As the prior art for causing more carbon dioxide to contact the living organism, (2) a carbon dioxide bathing device has been known. This emits and disperses carbon dioxide in hot water and dissolves it at the high density. When bathing in hot water dissolving carbon dioxide, the skin directly contacts it like the above mentioned bathing agent.

A blood circulation accelerating device (for example, Patent Document 1) has now been disclosed, which (3) attaches a cover to a human living organism on one part of his surface to form a sealed space together with his surface, and introduces carbon dioxide into the sealed space from a carbon dioxide supply means for carrying out a carbon dioxide bathing.

A carbon dioxide pressure bathing device which is equipped with at least (4) the carbon dioxide supply means, a pressurizing means, and a covering material for covering the living organism's skin and causing carbon dioxide to contact the skin at pressure of not less than predetermined value, has been proposed by an inventor of the present invention.

As the prior art for causing oxygen to be absorbed into the living organism, (5) a high density oxygen bathing device has been known. Being similar to the carbon dioxide bathing device, this emits and disperses oxygen dioxide in hot water, in which taking a bath, oxygen is caused to directly contact the skin.

CITATION LIST

Patent Document

Patent Document 1: Japanese Laid-Open Patent Publication No. 07-171189

SUMMARY OF INVENTION

Problems to be Solved by the Invention

However, each of the above prior arts (1), (2) and (5) dissolves carbon dioxide or oxygen in hot water when taking the bath, and causes carbon dioxide or oxygen to be absorbed into the skin of the living organism. Accordingly, they were involved with difficult points of using only when taking the bath. In addition, since carbon dioxide is easily dissolved in water, and even if much consuming it for dissolving in hot water, an absorption rate into the skin is never much high.

On the other hand, since the above prior arts (3) and (4) cause carbon dioxide to directly contact the living organism and if comparing with the prior arts (1) and (2), effects are high and efficiency is good. But these have not optimized to control the amounts or pressures of carbon dioxide, oxygen and the mist to be introduced into the shielding member (cover).

In view of the above mentioned problems, it is an object of the invention to provide a gas mist pressure bath system which is possible to control the amounts, pressures and others of gas and liquid, and cause the gas mist to be absorbed through the skin and mucous membrane of the human living organism under an optimum condition.

Means for Solving the Problem

For solving the above mentioned problems, the present invention is to provide a gas mist pressure bath system, in which a mist (called as "gas mist" hereafter) is prepared at a density of not less than a predetermined value by pulverizing and dissolving carbon dioxide or oxygen, otherwise a mixed gas (called as "gas" hereafter) of carbon dioxide and oxygen, and a liquid, and the thus prepared gas mist is contacted to the skin and mucous membrane of the living organism. The present system comprises a gas supply means, a liquid supply means, a gas mist supply means for storing inside the liquid, discharging the gas into the stored liquid, thereby to change the above mentioned liquid into fine liquid drops, and pressure-supplying the fine liquid drops under a condition of the mist pulverized and dissolved together with the gas, a covering member for covering the skin and mucous membrane of the living organism as well as forming a space for sealing inside the gas mist supplied from the gas mist supply means. Since the above mentioned gas supply means generates the gas mist, the gas supply means is composed of a first gas supply means for generating the gas mist by discharging the gas into the liquid stored in the gas mist supply means as well as a second gas supply means for dissolving the gas in the liquid by discharging the gas into the liquid stored in the gas mist supply means, and thus, the present system is characterized by contacting the gas mist within the living organism covering member to the skin and mucous membrane of the living organism at a pressure of not less than a predetermined value.

By the way, the invention refers it as "pulverizing and dissolving" to pulverize the liquid into fine liquid drops, and cause to contact and mix with gas (carbon dioxide, or oxygen, or a mixed gas of carbon dioxide and oxygen).

Herein, more desirably, the above mentioned gas mist pressure bath system of the invention is further provided with a sensor for measuring supplying conditions of the gas, liquid and gas mist, and control means for controlling supplies thereof based on the measuring values of the sensor.

In addition, the above gas mist pressure bath system is desirably further provided with a pressurizing means for pressurizing the living organism covering member.

The control means may supply the gas mist intermittently into the living organism covering member to perform interval pressurization (pulse pressurization) thereon. Otherwise, the pressurizing means may pressurize the living organism cover member intermittently to perform interval pressurization (pulse pressurization) thereon.

It is optimum that the above mentioned liquid is any one or plural combination of water, ionic water, physiological salt solution, ozone water, purified water or sterilized and purified water. Desirably, this liquid further contains any one or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, carcinostatic substance, anti-hypertensive agent, cosmetic agent, or trichogen.

Preferably, the liquid is supplied into the gas mist supply means under a condition of being heated. Sizes of the gas mist supplied from the gas mist supply means into the living organism covering member are suitably not more than 10 μm.

The control means preferably holds pressure at 1.02 to 2.5 air pressure in the living organism covering member when pressure-bathing of the gas mist.

There may be provided an electric charge supply means for supplying charge to the mist from the gas mist supply means. At this time, the charge is preferably minus.

Desirably, the gas mist supply means has a gas mist supply pipe for supplying the gas mist into the living organism covering member, and this gas mist supply pipe has a filter for removing liquid drops attached to the pipe inside. Further, a whole or one part of the gas mist supply pipe is suitably composed of a cornice shaped pipe, and this gas mist supply pipe is provided with a check valve.

In addition, the gas mist supply port of the living organism covering member is also provided at its supply port with the check valve.

Further, the gas mist supply means has a storage for storing the liquid and the gas mist. The storage is shaped in dome of convex having a curved face toward an upper portion and is formed with a gas mist discharge portion at the dome shaped top.

Further, the gas mist supply means has the storage for storing the liquid and the gas mist, and the storage has desirably one or plurality of pored plates for refining the gas mist.

The control means desirably stops the gas from the gas supply means when the pressurizing value within the living organism covering member is higher than a predetermined value.

Advantageous Effect of the Invention

According to the gas mist pressure bath system of the invention, since it is possible to control the amount and pressure of the gas mist in the pressure bathing cover for the living organism by the control device, the gas mist pressure bathing can be always taken under the best condition.

Further, pressurization into the pressure bathing cover for the living organism is easy, and skin-pass breathing of the gas can be carried out more efficiently.

BRIEF DESCRIPTION OF DRAWINGS

[FIG. 9] Typical views showing configuration examples (No. 1) of the pressure bathing covers for the living organism of the gas mist pressure bath system depending on the second embodiment of the invention;

[FIG. 11] A generally schematic view of the gas mist pressure bath system depending on a third embodiment of the invention.

DESCRIPTION OF EMBODIMENTS

In the following description, explanations will be made to embodiments of this invention, referring to the attached drawings.

First Embodiment

Figure 1:
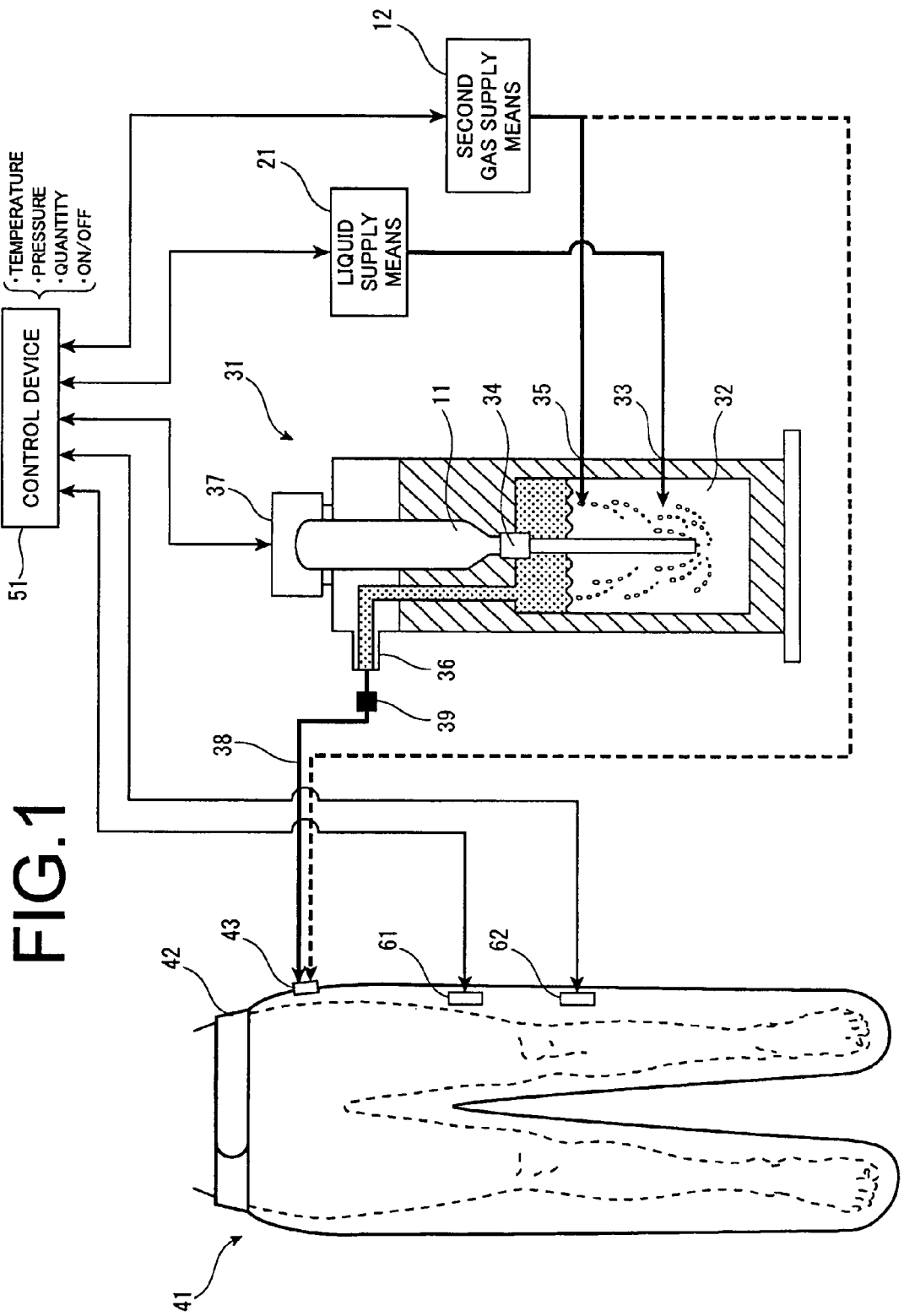
[FIG. 1] A generally schematic view of the gas mist pressure bath system depending on a first embodiment of the invention.

FIG. 1 is the generally schematic view of the gas mist pressure bath system depending on the first embodiment of the invention. As shown in this view, the gas mist pressure bath system of the present embodiment comprises a first gas supply means 11, a second gas supply means 12, a liquid supply means 21, a gas mist supply means 31 which stores a liquid inside thereof and injects into the stored liquid a gas (carbon dioxide, or oxygen, otherwise a mixed gas of carbon dioxide and oxygen) from the first gas supply means 11, thereby to generate a gas mist by pulverizing and dissolving the liquid and the gas, and supplying under pressure the gas mist, a pressure bathing cover 41 for the living organism of forming a space for sealing inside the supplied gas mist, and a control device 51 for generating and controlling to supply the gas mist ("the pressure bathing cover 41 for the living organism" will be referred sometimes to as only "the pressure bathing cover 41" hereafter).

The gas supply means 11, 12 supply the gas into the liquid stored in the gas mist supply device 31. Firstly, the first gas supply means 11 is served for generating the gas mist by injecting the gas at high pressure into the liquid stored in the gas mist supply device 31. On the other hand, the second gas supply means 12 is served for releasing the gas nearly the surface of the liquid stored in the gas mist supply device 31 for dissolving the gas in the stored liquid. In case the gas mist is enough supplied in the pressure bathing cover 41 for the living organism, only the gas is directly supplied from the second gas supply means 12 into the pressure bathing cover 41 for the living organism. As the gas supply means 11, 12, to use a gas bomb is optimum. Omitting illustration, the gas supply means 11, 12 are desirably disposed with respective regulators for adjusting pressure. Further omitting illustration, the gas supply means 11, 12 may be provided with heaters for heating the gas or thermometers for controlling temperature.

The liquid supply means 21 is composed of such as a pump and supplies water to the gas mist supply device 31. As the liquid, it is suitable to use water, ionic water, physiological salt solution, ozone water, purified water or sterilized water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hypertensive agent, cosmetic agent, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise, the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate. In addition, high density carbonate spring may be added (as examples organic components, sulfate, carbonate, sodium dichloroisocyanurate) having main components of carbonate and organic acid.

In the liquid supply means 21, it is desirable to dispose a heater (not shown) heating the liquid (for example, heating to a hot water of around 40° C.) or a thermometer (not shown) controlling temperature.

The gas mist supply device 31 is such a device which stores inside thereof the liquid supplied from the liquid supply means 21, discharges the gas of high pressure hereinto from the first gas supply means 11, thereby to change the liquid into fine liquid drops, generates the gas mist by pulverizing and dissolving together with the gas, and supplies the gas mist under pressure into the pressure bathing cover for the living organism. Further, the gas is supplied to the liquid stored inside thereof from the second gas supply means 12 to keep the gas dissolved. It is possible thereby to generate the gas mist having dissolved the gas at high density.

Figure 2:
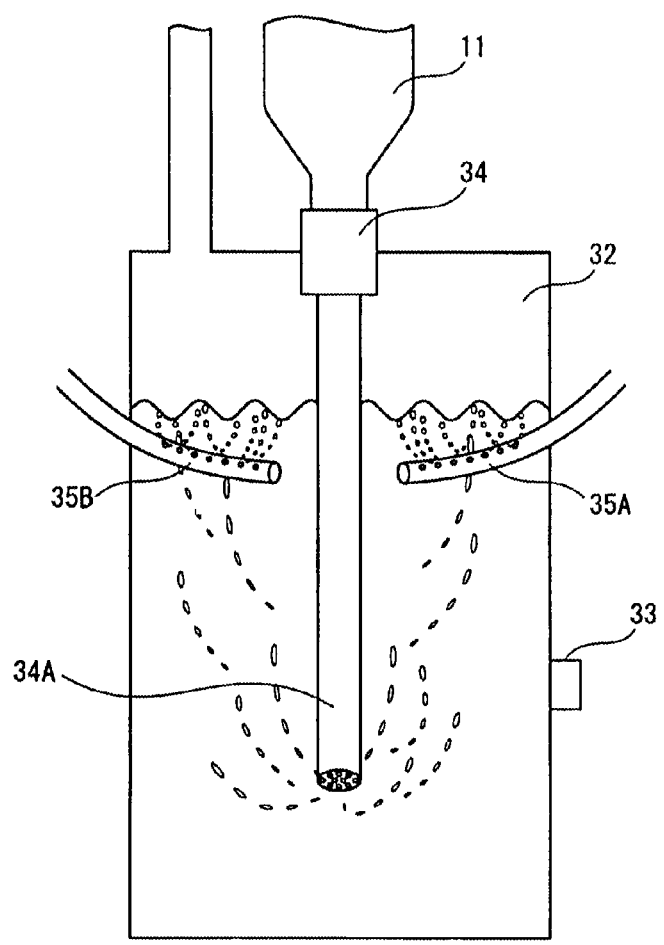
[FIG. 2] A typical view showing the concrete example of the mist generating part in the gas mist supply means of the gas mist pressure bath system of the invention.

FIG. 2 shows the concrete example of the mist generating part in the gas mist supply device 31. As shown in FIGS. 1 and 2, the gas mist supply device 31 is furnished with a storage 32 of storing the gas, liquid and gas mist, a liquid supply port 33 of supplying the liquid into the storage 32 from the liquid supply means 21, a first gas supply port 34 having a needle inside thereof for opening the first gas supply means 11 (herein, the small sized gas bomb of a cartridge system), a second gas supply port 35 of supplying to dissolve the gas from the second gas supply means 12 into the liquid in the storage 32, a gas mist discharge port 36 for discharging the gas mist generated within the storage 32, and a cap 37 for securing the gas bomb (the first gas supply means) 11 and urging the gas bomb 11 to the first gas supply port 34.

For generating the gas mist, at first, the liquid is poured from the liquid supply port 33 into the storage 32 and kept there, and the liquid supply port 33 is closed. By discharging the gas from the second gas supply means 12, the gas is dissolved in the liquid. The second gas supply port 35 is, as shown in FIG. 2, composed of two nozzles 35A, 35B having plural holes (gas jetting outlets) and discharges the gas nearly the liquid surface of the storage 32. Desirably, the nozzles 35A, 35B are, as shown in FIG. 2, disposed with declination to be lower-positioned toward front ends so that the gas can be discharged nearly the liquid surface even if the height of the liquid surface is changed. Subsequently, tightening the cap 37 under a condition of setting the gas bomb 11, the gas bomb 11 is pushed down, and the bomb is opened at its front end by the needle of the first gas supply port 34, and the gas is forcibly splashed and injected into the liquid from the nozzle 34A of the front end of the first gas supply port 34. As shown in FIG. 2, the nozzle 34A is formed at its front end with one or plural holes (gas jetting outlets). By the way, if furnishing a spring inside of the first gas supply port 34, such a structure may be realized which does not discharge the gas until more than a certain pressure. If injecting the gas at high pressure into the liquid, the gas mist occurs when generated bubbles blow up. Sizes of the mist generated at this time are desirably fine, and concretely, being less than 10 μm is optimum.

The generated gas mist spreads over inside of the storage 32 and is discharged from the gas mist discharge port 36 following a gas convection. Herein, the discharged gas mist is supplied into the pressure bathing cover 41 for the living organism via the gas mist supply pipe 38. A gas mist supply pipe 38 is connected to a supply port 43 of the pressure bathing cover 41 for the living organism. The gas mist supply pipe 38 has a liquid drop removing filter 39 for removing droplets attached to a pipe inside. Although not illustrating, the gas mist supply pipe 38 is provided inside with a check valve for checking back-flow of gas mist and gas.

Figure 3:
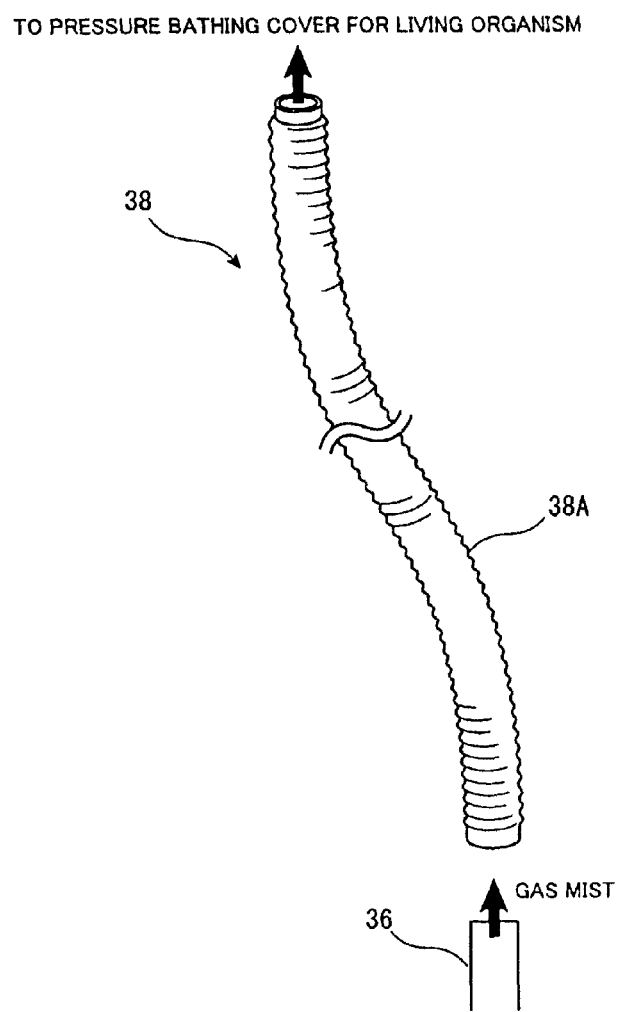
[FIG. 3] A typical view showing one example of the gas mist supply pipe used to the gas mist pressure bath system of the invention.

Further, as shown in FIG. 3, preferably, the gas mist supply pipe 38 is overall or partially composed of a soft cornice shaped pipe 38A of a large diameter. If composing with such a cornice shaped pipe 38A, the gas mist supply pipe 38 is freely bent and may be expanded so that a user of this system is not restricted in his action. Even if the gas mist flowing in the gas mist supply pipe 38 becomes gradually liquefied, the liquid can be removed through concave and convex of the cornice.

The structure of the gas supply means 11 is the small sized gas bomb of the cartridge type, but instead, it may employ a large sized gas bomb of a business operation.

Further, the storage 32 has a structure as shown in FIG. 1 having a substantially cylindrical shape with a level upper face, and it is also desirable that the storage 32 is shaped in convex dome toward an upper portion. In this case, the gas mist discharge port 36 is positioned at an almost head top of the dome. By shaping such a form, it is possible that the gas mist is more stored, while preventing that the mist contacts the top portion of the inside wall of the storage 32, reverting to the liquid and drops onto the bottom of the storage 32.

Figure 4:
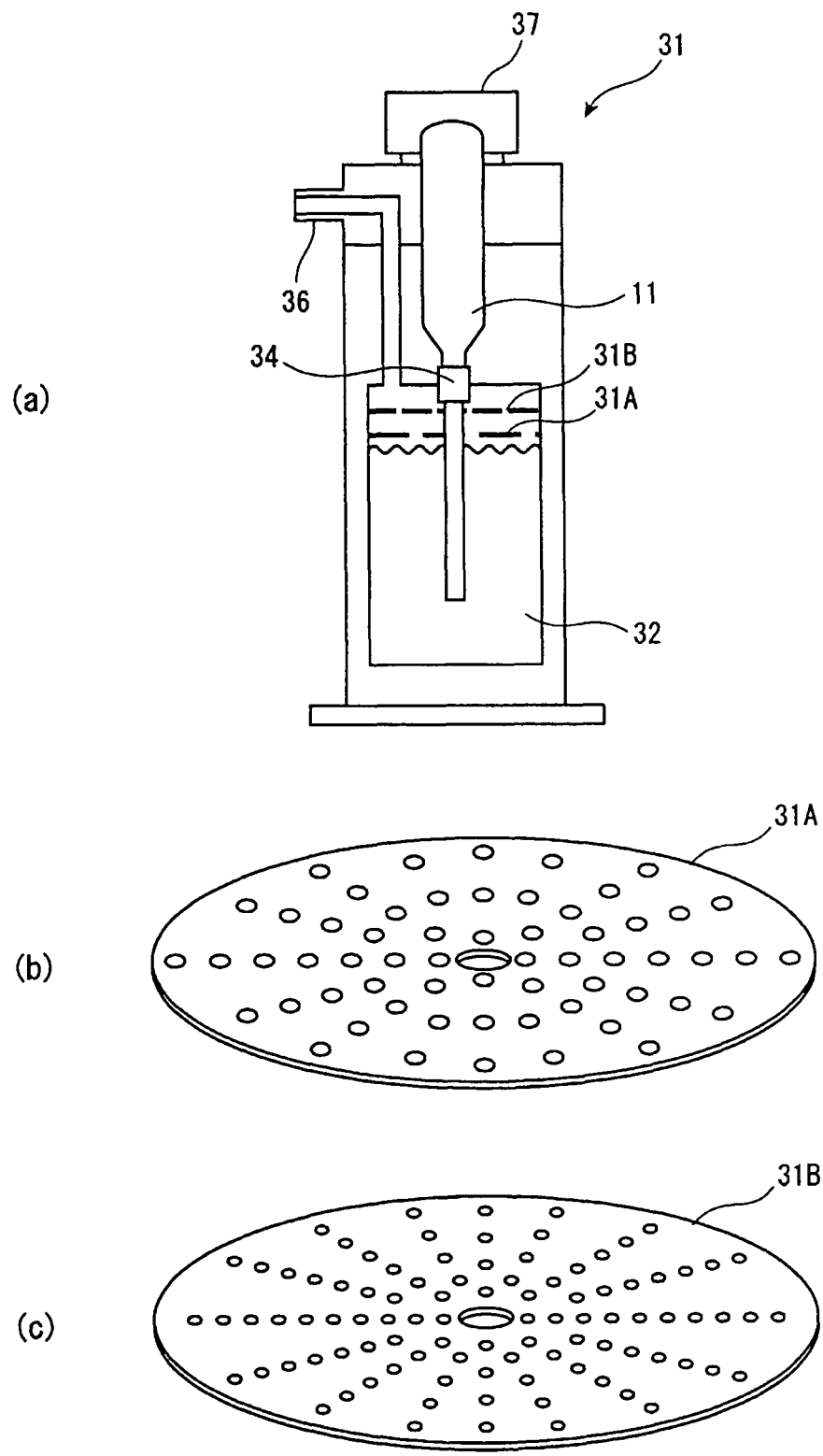
[FIG. 4] Typical views showing examples of plates to be placed within the gas mist supply device of the gas mist pressure bath system of the invention.

The storage 32 may be, as shown in FIG. 4(a), furnished inside with one sheet or plural sheets of plates 31A, 31B (in FIG. 4, as the example, two sheets). The plates 31A, 31B are, as shown in FIG. 4(b), (c), formed with plural pores, and the generated gas mist is further refined by passing through the pores. Then, with respect to the upper plate 31B and the lower plate 31A, it is preferable that the diameter of the pore of the upper plate 31B is smaller than that of the pore of the lower plate 31A.

The pressure bathing cover 41 for the living organism is a cover which enables to form a space for covering the skin and mucous membrane (herein, as the example, a lower extremity of the living organism) and to seal the gas mist and the gas inside. The pressure bathing cover 41 for the living organism is composed of a pressure resistant, non-air permeable and non-moisture permeable material, for example, preferably, the natural rubber, silicone rubber, polyethylene, polypropylene, polyvinylidene, polystylene, polyvinylacetate, polyvinyl chloride, polyamide resin, polytetrafluoroethylene. The pressure bathing cover 41 for the living organism has a supply port 43 for introducing the gas mist and the gas inside. The supply port 43 is inside provided with a check valve for checking back flow of the gas mist and the gas. The pressure bathing cover 41 may be provided with an opening or a valve for discharging the gas and the gas mist. The pressure control may be carried out manually, but desirably automatically by a control device 51 together with supply control of the gas and the gas mist on the basis of measuring values of a later mentioned manometer. A safety valve (recess valve) may be provided for automatically opening a valve when the inside of the pressure bathing cover 41 becomes more than a constant pressure.

The pressure bathing cover 41 for the living organism is inside installed with the manometer 61 for measuring an internal pressure. The control device 51 controls supply of the gas mist and the gas on the basis of measuring values of the manometer 61 for maintaining a pressure value within the pressure bathing cover 41 to be more than 1 air pressure (more preferably, around 1.02 to 2.5 air pressure). For example, the control device 51 controls or stops the supply of the gas or gas mist from the gas supply means 11, 12 and the gas mist supply device 31 or discharges the gas or gas mist from the pressure bathing cover 41. Further, the pressure bathing cover 41 for the living organism is inside installed with a thermometer 62 for measuring a temperature within the pressure bathing cover 41 for the living organism. The control device 51 performs on-off of a heater installed in the liquid supply means 21 on the basis of measuring values of the thermometer 62 for maintaining a pre-determined temperature (for example, around 38° C.) bringing about warm bath effects within the pressure bathing cover 41.

The pressure bathing cover 41 for the living organism has, around its opening, a stopper 42 for attaching to and detaching from the living organism (herein, as the example, the lower extremity of the living organism) and for stopping leakage of the gas mist and the gas. The stopper 42 is suitably composed of, e.g., a face stretching fastener, or may have a sole string or rubber or their combination. For heightening a sealing property in the pressure bathing cover 41 for the living organism, the inside (that of the stopper 42) may have a material attaching to the user's skin. The adhesive material is preferably, e.g., a visco-elastic gel of polyurethane or silicone rubber. Further this adhesive material is detachably used and exchangeable each time or if viscosity becomes weak.

The control device 51 is composed of a computer having CPU, memory and display. This device 51 performs various kinds of controls for carrying out the gas mist pressure bath under the optimum condition, such as pressure control of or on-off switch of the gas supplied from the gas supply means 11, 12, supply and switch of the gas into the gas mist supply device 31/the pressure bathing cover 41 for the living organism, controls of supplying pressure or temperature of the liquid from the liquid supply means 21, or on-off switch of the gas mist. In particular, preferably, when the pressure value becomes more than a predetermined value in the pressure bathing cover 41 for the living organism, such a structure is composed to stop supplying the gas from the gas supply means 11, 12 by the control device 51.

For carrying out the gas mist pressure bathing by using the gas mist pressure bath system of the present embodiment, the pressure bathing cover 41 for the living organism is secured to the living organism (herein, as the example, the lower extremity) and closed. Into the gas mist supply device 31, the liquid is supplied from the liquid supply means 21, and next, into this liquid, the gas is supplied from the second gas supply means 12 for causing the gas to be dissolved in the liquid. Next, the gas is injected into the liquid from the first gas supply means 11 to generate the gas mist. Then, the control device 51 controls the supplying pressures, amounts, or temperatures of the liquid and the gas. The generated gas mist is supplied from the supply port 43 into the pressure bathing cover 41. If the mist is enough filled in the pressure bathing cover 41, only the gas is directly supplied from the second gas supply means 12 into the pressure bathing cover 41. When the inside of the pressure bathing cover 41 for the living organism becomes an optimum pressurized and heated condition (around 1.02 to 2.5 air pressure and around 38° C.) in view of the measuring values of the manometer 61 and the thermometer 62, the control device 51 once stops supply of the gas mist or the gas, and under this condition the gas mist pressure bath is carried out.

The above mentioned explanation has been made with the example of the lower extremities of the human living organism, and the invention is applicable to various parts. Then, the optimum gas mist pressure bathing is performed, employing forms of the pressure bathing cover 41 for the living organism meeting object parts of the living organism.

Figure 5:
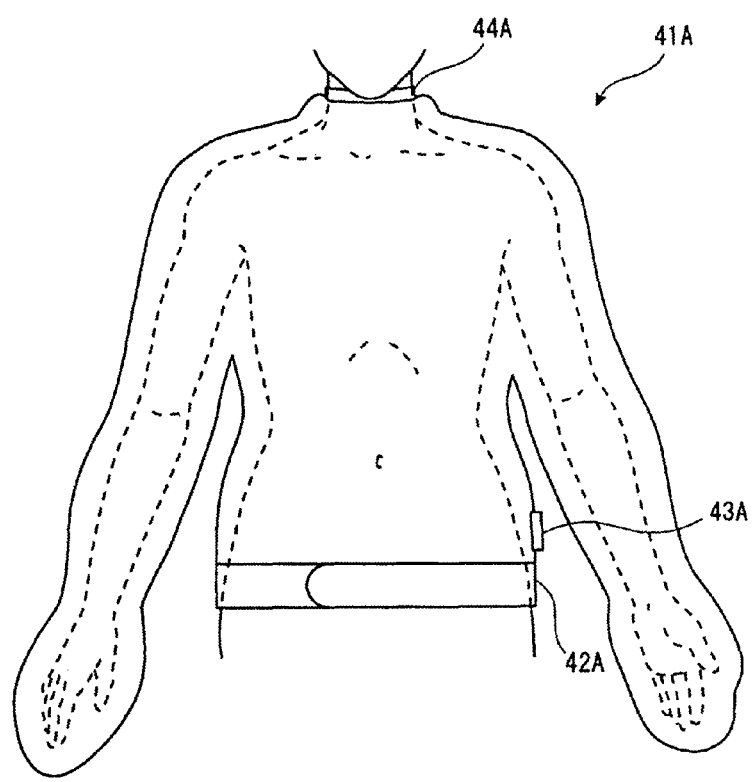
[FIG. 5] A typical view showing a configuration example (No. 1) of the pressure bathing cover for the living organism of the gas mist pressure bath system depending on the first embodiment of the invention.
Figure 6:
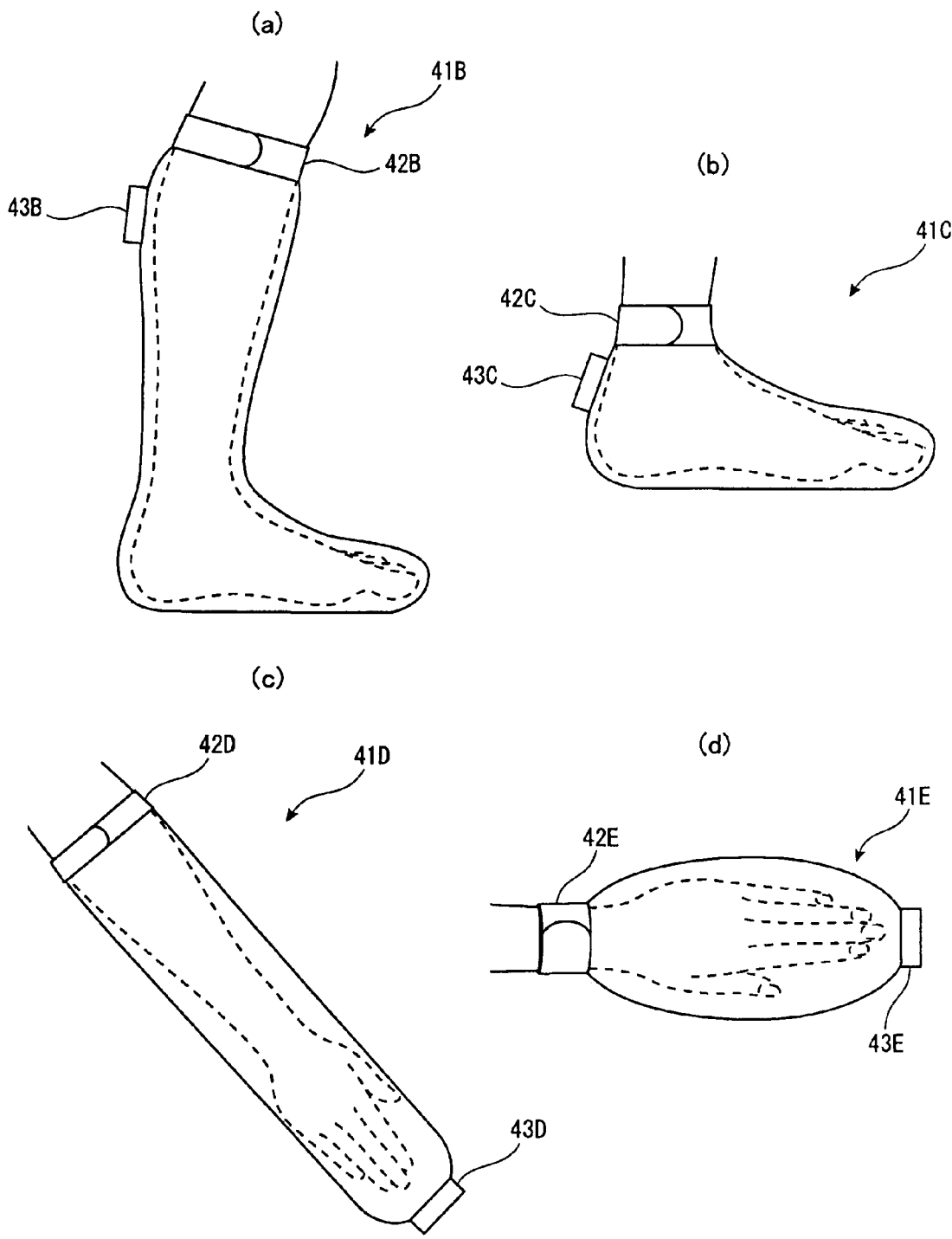
[FIG. 6] Typical views showing configuration examples (No. 2) of the pressure bathing covers for the living organism of the gas mist pressure bath system depending on the first embodiment of the invention.
Figure 7:
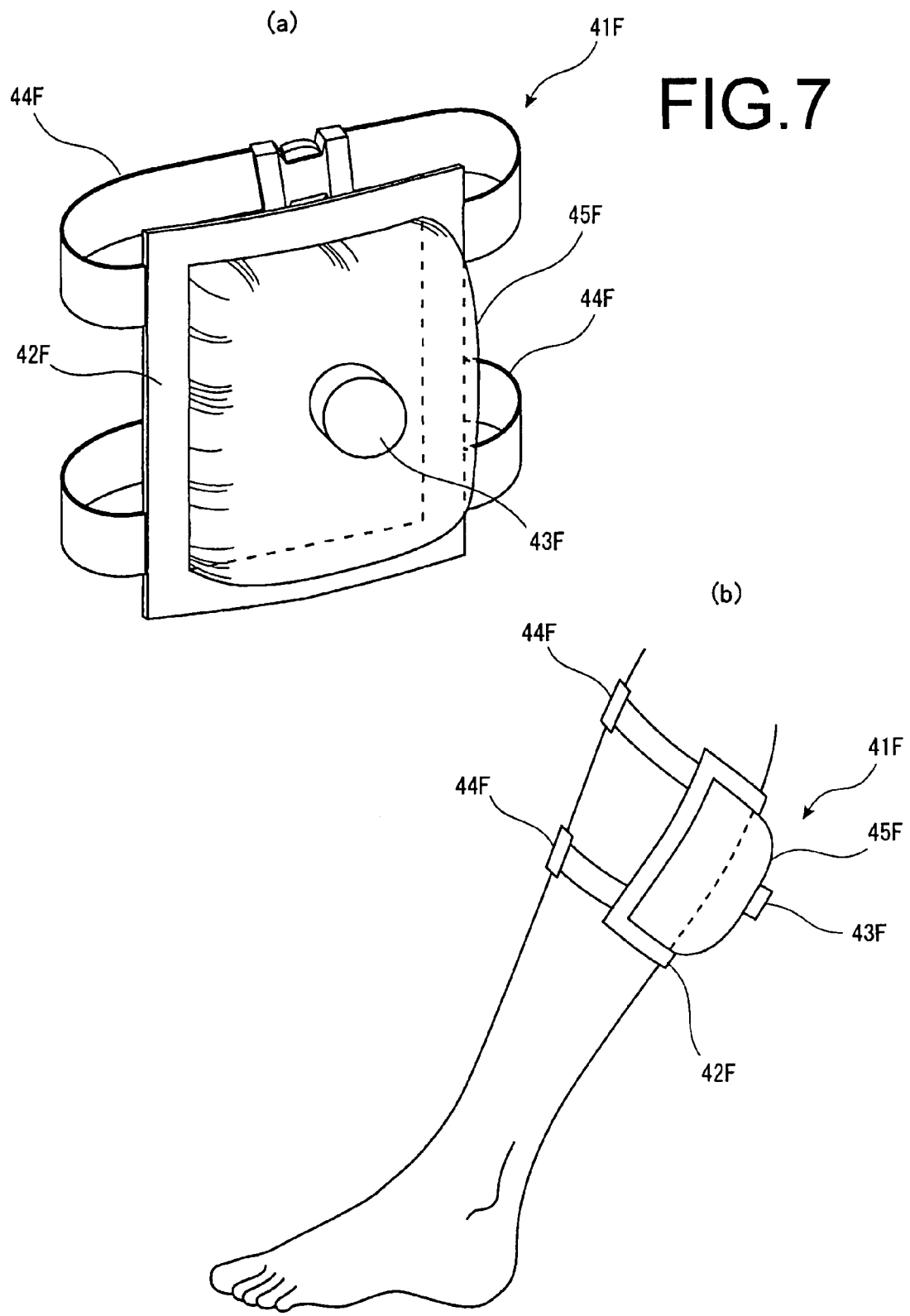
[FIG. 7] Typical views showing configuration examples (No. 3) of the pressure bathing covers for the living organism of the gas mist pressure bath system depending on the first embodiment of the invention.

FIGS. 5 to 7 show the various shaped examples of the pressure bathing cover 41 for the living organism. At first, FIG. 5 shows the schematic view of the pressure bathing cover 41A for the upper half of the living organism. The pressure bathing cover 41A has a shape for wrapping the whole of the upper half of the living organism, and has a stopper 42A for easily attaching to and detaching from the living organism at the opening of a waist part and stopping leakage of the gas mist and the gas. A similar stopper 44A is formed around the opening of a neck. 43A designates a supply port for introducing the gas mist and the gas inside.

FIG. 6 shows the various shaped examples of the pressure bathing covers 41 covering further limited parts of the living organism. FIG. 6(*a*) is the pressure bathing cover 41B for one-side lower extremity (lower part under a knee) of the living organism. The pressure bathing cover 41B has the stopper 42B at its opening portion and a supply port 43B for introducing inside the gas mist and the gas. FIG. 6(*b*) is the pressure bathing cover 41C for a foot. The pressure bathing cover 41C has a stopper 42C at its opening portion and a supply port 43C for introducing inside the gas mist and the gas. FIG. 6(*c*) is the pressure bathing cover 41D for a forearm. The pressure bathing cover 41D has a stopper 42D and a supply port 43D for introducing inside the gas mist and the gas. FIG. 6(*d*) is the pressure bathing cover 41E for a hand. The pressure bathing cover 41E has a stopper 42E and a supply port 43E for introducing inside the gas mist and the gas.

Further, FIG. 7 shows a patch shaped pressure bathing cover 41F. FIG. 7(*a*) is a view showing the outline of the patch shaped pressure bathing cover 41F. FIG. 7(*b*) is a view showing an external appearance when attaching the patch shaped pressure bathing cover 41F to the living organism (herein, the lower extremity). The pressure bathing cover 41F is composed of a cover part 45F for covering the skin and mucous membrane of the living organism, a stopper 42F provided at the margin of the cover part 45F and directly attached to the skin and mucous membrane, a supply port 43F for supplying the gas mist and the gas into the space defined by the cover part 45F and the stopper 42F, and fasteners 44F made of belts or strings for fastening the cover part 45F to the living organism.

In regard to the pressure bathing cover 41, other than the examples shown in FIGS. 5 to 7, various shapes may be assumed. In sum, if forming the space for sealing inside the gas mist and the gas, any shape is sufficient. An air discharge port may be formed for discharging the gas mist and the gas from the inside of the pressure bathing cover 41. In addition, the invention may be applied not only to the human living organism but also to animals.

In addition, since pressurization in the gas mist pressure bath heightens the effects by pressurizing in pulsing at predetermined interval, the control device 51 may supply the gas mist into the pressure bathing cover 41 for the living organism intermittently at fixed rhythm. As to the pressurizing interval at such a case, if synchronizing with pulsations, the effects are more heightened.

Second Embodiment

Figure 8:
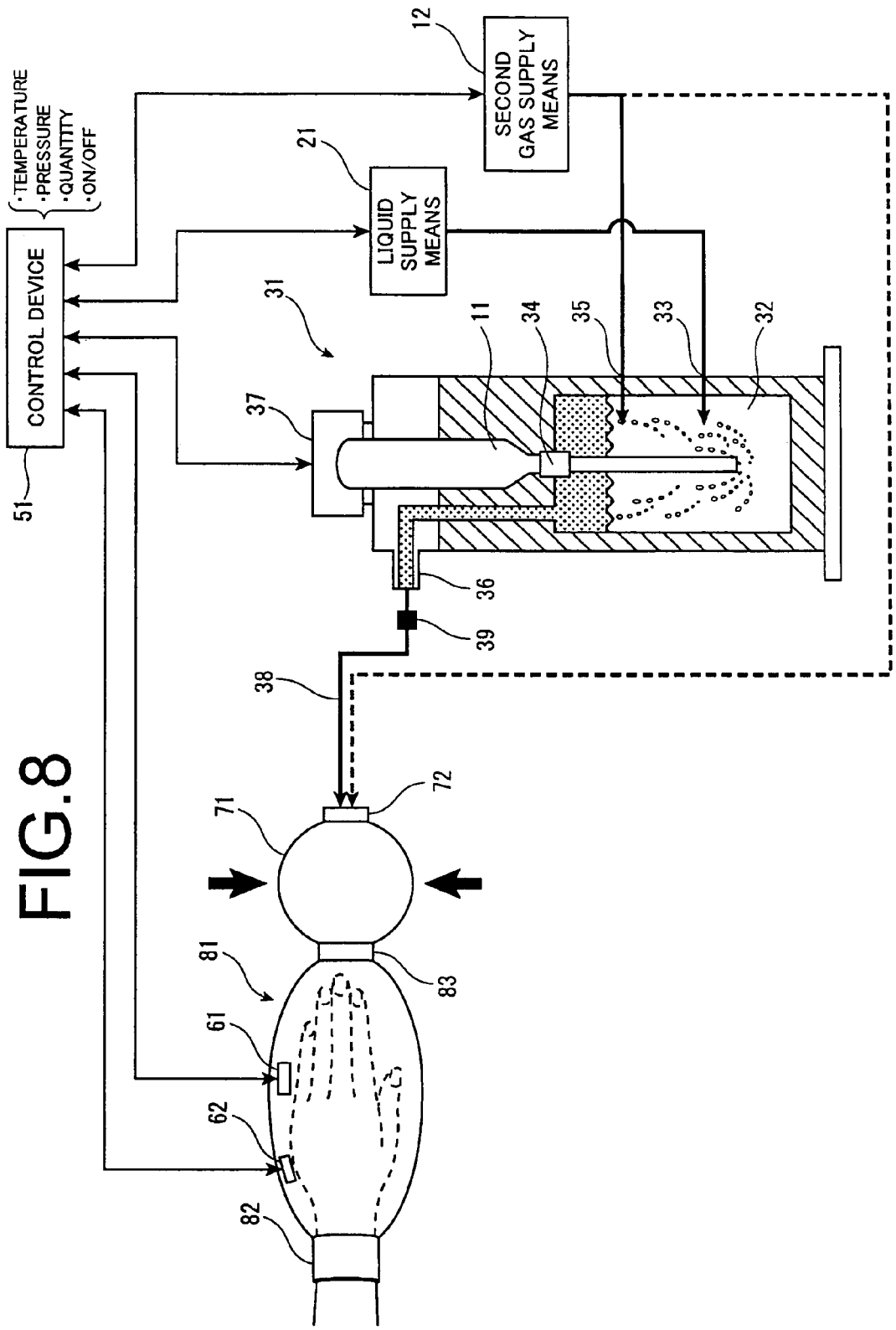
[FIG. 8] A generally schematic view of the gas mist pressure bath system depending on a second embodiment of the invention.

FIG. 8 is the generally schematic view of the gas mist pressure bath system depending on the second embodiment of this invention. This embodiment will explain the gas mist pressure bath system further having a pressurizing means for simplifying pressurization within the pressure bathing cover for the living organism. As to the same parts as those of the first embodiment shown in FIG. 1, the same numerals will be given, and detailed explanation will be omitted.

As shown in FIG. 8, the gas mist pressure bath system of this embodiment has the pressure bathing cover 81 for the living organism forming a space into which the gas mist and the gas are sealed and a pressurizing part (gas storage) 71 connecting the pressure bathing cover 81 for carrying out pressurization therein.

The pressure bathing cover 81 has almost the same structure of the pressure bathing cover 41 shown in the first embodiment, and has the stopper 82 and the gas mist and gas supply port 83, provided herein that the supply port 83 is connected to the pressurizing part 71. By the way, the example hereof illustrates the pressure bathing cover 81 of a shape for covering a hand of the living organism.

The pressurizing part 71 is the gas storage being hollow connecting the pressure bathing cover 81 because of carrying out pressurization therein. The pressurizing part 71 is connected to the supply port 83 of the pressure bathing cover 81 and has also the supply port 72 of itself from which the gas mist or the gas are supplied inside. The supply port 72 of the pressurizing part 71 is also provided with the check valve for checking back flow of the gas mist and the gas. After storing the gas mist or the gas in the pressurizing part 71, if pressurizing as crushing the pressurizing part 71 as showing with arrows, since the gas mist or the gas in the pressurizing part 71 are discharged as escaping into the pressure bathing cover 81, its inside can be pressurized.

The pressurizing part 71 may be structured as pressing manually, and mechanically by controlling the control device 51 using a driving device or the like. As mentioned above, pressurization in the gas mist pressure bath system heightens effects by performing interval pressurization in pulse, and so the pressurizing part 71 may be pressed intermittently. The pressurizing interval heightens effects by synchronizing with pulsation of pulse.

For carrying out the pressure bathing by using the gas mist pressure bath system of the present embodiment, the pressure bathing cover 81 is secured to the living organism (herein, as the example, the hand) and closed. To the gas mist supply device 31, the liquid is supplied from the liquid supply means 21, and subsequently, the gas is supplied into this liquid from the second gas supply means 12. Next, the gas is injected into the liquid from the first gas supply means 11 to generate the gas mist. At this time, the control device 51 adjusts the supplying pressures, amounts or temperatures of the liquid and the gas. The generated gas mist is supplied from the supply port 83 via the pressurizing part 71 into the pressure bathing cover 81 for the living organism. When the mist is enough filled in the pressure bathing cover 81 for the living organism, only the gas is directly supplied from the second gas supply means 12 into the pressure bathing cover 81 for the living organism via the pressurizing part 71.

Thereby, in the gas mist supply device 31, the gas mist is generated by the fluid nozzle, and the generated gas mist is supplied from the supply port 83 into the pressure bathing cover 81 for the living organism via the pressurizing part 71. When the mist is enough filled in the pressure bathing cover 81, only the gas is directly supplied from the second gas supply means 12 into the pressure bathing cover 81 for the living organism via the pressurizing part 71. The control device 51 so controls that the inside of the pressure bathing cover 81 is to be at an optimum temperature (for example, around 38° C.) from the measuring values of the thermometer 62. When the gas mist or the gas of the optimum amount is stored in the pressure bathing cover 81 and the pressurizing part 71, the pressurizing part 71 is pressurized as crushed. Thereby, the gas mist or the gas in the pressurizing part 71 are discharged into the pressure bathing cover 81, and the inside of the pressure bathing cover 81 for the living organism is pressurized moderately (around 1.02 to 2.5 air pressure) and the gas mist pressure bath is carried out.

As having mentioned in the first embodiment, since the pressure bathing cover 81 is applied to various parts of the living organism, various shapes may be used, provided in this embodiment that shapes (size) must be easily pressurized by the pressurizing part 71. This substantially depends on the dimension of the pressurizing part 71. Actually, so far as pressurizing means are any one, the pressurizing part 71 is desirably compact as not demanding large spaces, and accordingly, the pressure bathing cover for the living organism is also desirably applied to comparatively compact objects (covering the limited parts of the living organism).

Figure 10:
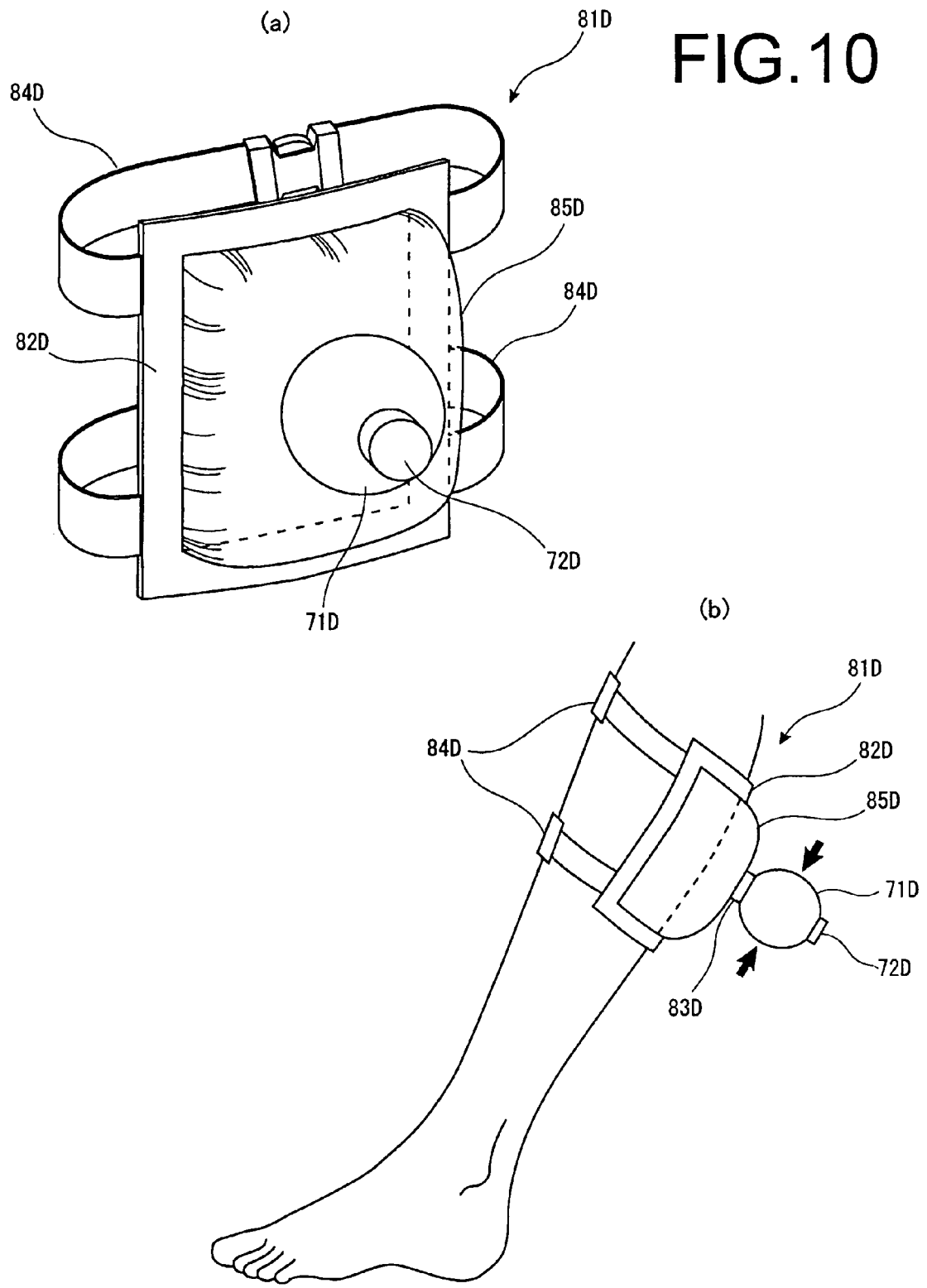
[FIG. 10] Typical views showing configuration examples (No. 2) of the pressure bathing covers for the living organism of the gas mist pressure bath system depending on the second embodiment of the invention.

FIGS. 9 and 10 show examples of the pressure bathing cover 81 for the living organism and the pressurizing part 71 connected thereto. FIG. 9(*a*) is a pressure bathing cover 81A for one-side lower extremity (lower part under the knee of the living organism). The pressure bathing cover 81A has the stopper 82A at its opening portion and the supply port 83A for introducing inside the gas mist and the gas. The supply port 83A is connected to the pressurizing part 71, so that the gas mist and the gas are supplied into the pressure bathing cover 81A through the supply port 72A of the pressurizing part 71A. FIG. 9(*b*) is the pressure bathing cover 81B for the foot part of the living organism. The pressure bathing cover 81B has the stopper 82B at its opening and the supply port 83B for introducing the gas mist and the gas into the inside thereof. The supply port 83B is connected to the pressurizing part 71B, and the gas mist and the gas are supplied into the pressure bathing cover 81B through the supply port 72B of the pressurizing part 71B. FIG. 9(*c*) is the pressure bathing cover 81C for a forearm part of the living organism. The pressure bathing cover 81C is provided with the stopper 82C and with the supply port 83C for introducing the gas mist and the gas into the inside thereof. The supply port 83C is connected to the pressurizing part 71C, and the gas mist and the gas are supplied into the pressure bathing cover 81C through the supply port 72C of the pressurizing part 71C.

FIG. 10 shows the patch shaped pressure bathing cover 81D. FIG. 10(*a*) is a view showing the outline of the patch shaped pressure bathing covers 81D of the living organism. FIG. 10(*b*) is a view showing an external appearance when attaching the patch shaped pressure bathing cover 81D to the living organism (herein, the lower extremity of the living organism). The pressure bathing cover 81D is composed of the cover part 85D for covering the skin and mucous membrane of the living organism, the stopper 82D provided at the margin of the cover part 85D and directly attached to the skin and mucous membrane, the supply port 83D for supplying the gas mist and the gas into the space defined by the cover 85D and the stopper 82D, and fasteners 84D made of belts or strings for fastening the cover part 85D to the living organism.

The supply port 83D is connected to the pressurizing part 71D, and through the supply port 72D of the pressurizing part 71D, the gas mist and the gas are supplied into the pressure bathing cover 81D for the living organism.

An discharge port may be formed for discharging the gas mist and the gas from the inside of the pressure bathing cover 81 for the living organism. In addition, the invention may be applied not only to the humans but also to animals.

In the above embodiment, the pressurizing part 71 is the hollow gas storage connected to the pressure bathing cover 81 for the living organism, and so far as materials of easily pressurizing as crushing externally the pressure bathing cover 81 itself, any materials are sufficient.

Third Embodiment

FIG. 11 is the generally schematic view of the gas mist pressure bath system depending on the third embodiment of this invention. This embodiment will further explain the gas mist pressure bath system having a means for charging the generated mist As to the same parts as those of the first embodiment shown in FIG. 1, the same numerals will be given, and detailed explanation will be omitted.

As shown in FIG. 11, the gas mist pressure bath system of this embodiment is arranged with an electrode 92 at the gas mist discharge port 36 of the gas mist supply device 31. The electrode 92 is connected to a power supply device 91, and the control device 51 sets voltage values and performs on-off control.

The electrode 92 supplies an electric charge (minus charge is desirable) when discharging the mist generated by the gas mist supply device 31 from the gas mist discharge port 36. Thereby, the mist is made turn out charged so that adhesion to a charged material can be heightened. For example, if adhesion to the skin and the mucous membrane of the living organism, an effect of increasing absorption of the gas by the mist is further heightened, and if the mist contains medicines as above mentioned, penetration into the skin and the mucous membrane can be accelerated.

For carrying out the gas mist pressure bathing by using the gas mist pressure bath system of the present embodiment, the pressure bathing cover 41 is secured to the living organism (herein, as the example, the hand) and closed. To the gas mist supply device 31, the liquid is supplied from the liquid supply means 21, and subsequently, the gas is supplied into this liquid from the second gas supply means 12. Next, the gas is injected into the liquid from the first gas supply means 11 to generate the gas mist. At this time, the control device 51 adjusts the supplying pressure, amount or temperatures of the liquid and the gas. Further, the control device 51 turns on the power supply device 91 and supplies the charge to the mist from the electrode 92. The generated gas mist is supplied from the supply port 43 into the pressure bathing cover 41 for the living organism. When the mist is enough filled in the pressure bathing cover 41, only the gas is directly supplied from the second gas supply means 12. When the inside of the pressure bathing cover 41 becomes optimum pressure and heated condition (around 1.02 to 2.5 air pressure) from the measuring values of the manometer 61 and the thermometer 62, the control device 51 once stops supplies of the gas mist or the gas, and the gas mist pressure bathing is carried out.

With the structure as mentioned above, according to the gas mist pressure bath system of the invention, since it is possible to control the amount, pressure and other of the gas mist within the pressure bathing cover for the living organism by the control device, the gas mist pressure bath can be always carried out under the optimum condition.

Further, pressurization into the pressure bathing cover for the living organism is easy, the gas skin-pass absorption can be more efficiently performed.

The above explanation has been made to the embodiments of the invention, but the invention is not limited thereto, and so far as not deviating from the subject matter of the invention, various kinds of embodiments are, of course, available.

INDUSTRIAL APPLICABILITY

Thus, the present invention relates to the gas mist pressure bath device, in which the gas mist is prepared by pulverizing and dissolving the gas and the liquid, and the gas mist is directly contacted to the skin or mucous membrane of the living organism at pressure more than the predetermined value, and has an industrial applicability.

DESCRIPTION OF SYMBOLS

11: first gas supply means
12: second gas supply means
21: liquid supply means
31: gas mist supply device
32: storage
33: liquid supply port
34: first gas supply port
34A, 35A, 35B: nozzle
35: second gas supply port
36: gas mist discharge port
37: cap
38: gas mist supply pipe
38A: cornice shaped pipe
39: liquid drop removing filter
41, 41A, 41B, 41C, 41D, 41E, 41F, 81, 81A, 81B, 81C, 81D: pressure bathing cover for the living organism
42, 42A, 42B, 42C, 42D, 42E, 42F, 44A, 82, 82A, 82B, 82C, 82D: stopper
43, 43A, 43B, 43C, 43D, 43E, 43F, 83, 83A, 83B, 83C, 83D: supply port
44F: fastener
45F: cover part
51: control device
61: manometer
62: thermometer
71, 71A, 71B, 71C, 71D: pressurizing part
72, 72A, 72B, 72C, 72D: supply port
84D: fastener
85D: cover part
91: power supply device
92: electrode

The invention claimed is:

1. A gas mist pressure bath system, comprising:
a gas supply device for supplying carbon dioxide or a mixed gas of the carbon dioxide and oxygen;
a liquid supply device;
a gas mist supply device for storing the liquid supplied from the liquid supply device inside, discharging gas supplied from the gas supply device into the stored liquid, thereby to change the liquid into fine liquid drops and to generate gas mist including the gas by dissolving the gas in the fine liquid drops, and pressure-supplying the generated gas mist; and
a living organism covering member for covering a skin and a mucous membrane of a living organism, and forming a space for sealing inside the gas mist supplied from the gas mist supply device,
wherein the gas supply device includes a first gas supply device for discharging the gas into the liquid stored in the gas mist supply device to generate the gas mist, and a second gas supply device for discharging the gas into the liquid stored in the gas mist supply device to dissolve the gas in the liquid, and
wherein the gas mist within the covering member is contacted to the skin and the mucous membrane of the living organism.

2. A gas mist pressure bath system as set forth in claim 1, further comprising:
a sensor for measuring supplying conditions of the gas, the liquid and the gas mist, and
a control device for controlling supplies of the gas, the liquid and the gas mist based on the measuring values of the sensor.

3. A gas mist pressure bath system as set forth in claim 1, further comprising a pressurizing device for pressurizing the living organism covering member.

4. A gas mist pressure bath system as set forth in claim 2, wherein the control device supplies the gas mist intermittently into the living organism covering member to perform interval pressurization thereon.

5. A gas mist pressure bath system as set forth in claim 3, wherein the pressurizing device pressurizes the living organism cover member intermittently to perform interval pressurization thereon.

6. A gas mist pressure bath system as set forth in claim 1, wherein the liquid is at least one selected from the group consisting of water, ionic water, physiological salt solution, ozone water, purified water, and, sterilized and purified water.

7. A gas mist pressure bath system as set forth in claim 6, wherein the liquid contains at least one selected from the group consisting of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, carcinostatic substance, anti-hypertensive agent, cosmetic agent, and trichogen.

8. A gas mist pressure bath system as set forth in claim 6, wherein the liquid is supplied into the gas mist supply device under a condition of being heated.

9. A gas mist pressure bath system as set forth in claim 1, further comprising: an electric charge supply device for supplying electric charge to the gas mist supplied from the gas mist supply device.

10. A gas mist pressure bath system as set forth in claim 9, wherein the charge is negative charge.

11. A gas mist pressure bath system as set forth in claim 1, wherein the gas mist supply device includes a gas mist supply pipe for supplying the gas mist into the living organism covering member, and
the gas mist supply pipe contains a filter for removing liquid drops attached to the pipe inside.

12. A gas mist pressure bath system as set forth in claim 1, wherein the gas mist supply device includes a gas mist supply pipe for supplying the gas mist into the living organism covering member, and
at least one part of the gas mist supply pipe is a cornice shaped pipe.

13. A gas mist pressure bath system as set forth in claim 1, wherein the gas mist supply device includes a gas mist supply pipe for supplying the gas mist into the living organism covering member, and the gas mist supply pipe contains a check valve.

14. A gas mist pressure bath system as set forth in claim 1, wherein a gas mist supply port of the living organism covering member includes a check valve.

15. A gas mist pressure bath system as set forth in claim 1, wherein the gas mist supply device includes a storage for storing the liquid and the gas mist, and the storage is shaped in dome of convex having a curved face toward an upper portion and contains a gas mist discharge portion at a top of the dome.

16. A gas mist pressure bath system as set forth in claim 1, wherein the gas mist supply device includes a storage for storing the liquid and the gas mist, and the storage contains a plate with a pore for refining the gas mist.

17. A gas mist pressure bath system as set forth in claim 1, wherein the second gas supply device discharges the gas near a surface of the liquid, and the first gas supply device discharges the gas at a position that is lower than a position where the second gas supply device discharges the gas.

18. A gas mist pressure bath system as set forth in claim 1, wherein a gas discharging outlet of the first gas supply device is located at a position that is lower than a position of a gas discharging outlet of the second gas supply device.

19. A gas mist pressure bath system as set forth in claim 3, wherein the pressurizing device includes a storage storing the gas mist supplied from the gas mist supply device, the storage communicates with the living organism covering member, the storage is pressed inward by an outside thereof, and the storage exhausts the gas mist stored therein to the living organism covering member when being pressed, thereby the living organism covering member is pressurized.

20. A gas mist pressure bath system as set forth in claim 1, wherein the gas mist supply device includes a storage for storing the liquid and the gas mist, the storage contains an upper plate with pores and a lower plate with pores, and a diameter of the each pore of the upper plate is smaller than a diameter of the each pore of the lower plate.

\* \* \* \* \*